United States Patent

Mensink et al.

(10) Patent No.: US 8,789,950 B2
(45) Date of Patent: Jul. 29, 2014

(54) CONFOCAL LINE-SCANNING OPHTHALMOSCOPE

(75) Inventors: Michiel Herman Mensink, The Hague (NL); Julien Coyne, The Hague (NL)

(73) Assignee: I-Optics B.V., The Hague (NL)

( * ) Notice: Subject to any disclaimer, the term of this patent is extended or adjusted under 35 U.S.C. 154(b) by 0 days.

(21) Appl. No.: 13/807,942

(22) PCT Filed: Jul. 6, 2011

(86) PCT No.: PCT/NL2011/050485
§ 371 (c)(1),
(2), (4) Date: Jan. 2, 2013

(87) PCT Pub. No.: WO2012/005579
PCT Pub. Date: Jan. 12, 2012

(65) Prior Publication Data
US 2013/0176535 A1 Jul. 11, 2013

Related U.S. Application Data

(60) Provisional application No. 61/361,717, filed on Jul. 6, 2010.

(30) Foreign Application Priority Data

Aug. 23, 2010 (NL) .................................. 2005253

(51) Int. Cl.
*A61B 3/10* (2006.01)
*A61B 3/14* (2006.01)

(52) U.S. Cl.
USPC ........................................ 351/221; 351/206

(58) Field of Classification Search
USPC ................................................. 351/200–246
See application file for complete search history.

(56) References Cited

U.S. PATENT DOCUMENTS

| 4,765,730 A | 8/1988 | Webb |
| 4,768,873 A | 9/1988 | Webb |
| 4,768,874 A | 9/1988 | Webb et al. |

(Continued)

FOREIGN PATENT DOCUMENTS

| DE | 102006010105 A1 | 8/2007 |
| EP | 0314471 A1 | 5/1989 |

(Continued)

OTHER PUBLICATIONS

English Machine Translation of DE 102006010105 A1, dated Dec. 17, 2012.

(Continued)

*Primary Examiner* — Mohammed Hasan
(74) *Attorney, Agent, or Firm* — Hoffmann & Baron, LLP

(57) ABSTRACT

A line-scanning ophthalmoscope includes a light source to provide a light beam to an object of interest, a beam separating device to receive the light beam, provide the light beam to a scanning device and substantially separate the light beam and the returning light beam from the object of interest, a scanning device to direct the light beam to the object of interest for scanning the object of interest; to receive the light beam returning from the object of interest; and to direct at least part of the reflected light beam towards a detector; and a further scanning device to convert the light beam to a line-shaped light beam.

17 Claims, 9 Drawing Sheets

(56) References Cited

U.S. PATENT DOCUMENTS

| | | | |
|---|---|---|---|
| 5,353,073 | A | 10/1994 | Kobayashi |
| 6,331,059 | B1 | 12/2001 | Kudryashov et al. |
| 8,201,943 | B2 * | 6/2012 | Hammer et al. .............. 351/206 |
| 2002/0149746 | A1 * | 10/2002 | Eikelboom et al. ........... 351/221 |
| 2003/0231285 | A1 * | 12/2003 | Ferguson ...................... 351/221 |
| 2004/0207811 | A1 | 10/2004 | Elsner |
| 2005/0237615 | A1 | 10/2005 | Urey et al. |
| 2007/0252951 | A1 | 11/2007 | Hammer et al. |
| 2009/0257024 | A1 | 10/2009 | Luther et al. |

FOREIGN PATENT DOCUMENTS

| | | |
|---|---|---|
| EP | 0615721 A1 | 9/1994 |
| NL | 1024082 C1 | 2/2005 |
| WO | WO 2008/087012 A1 | 7/2008 |

OTHER PUBLICATIONS

English Abstract of NL 1024082 C1.

English Machine Translation of WO 2008087012 A1, dated Dec. 17, 2012.

* cited by examiner

CONFOCAL LINE-SCANNING OPHTHALMOSCOPE

CROSS-REFERENCE TO RELATED APPLICATIONS

This application is the National Stage of International Application No. PCT/NL2011/050485, filed Jul. 6, 2011, which claims the benefit of Netherlands Application No. 2005253, filed Aug. 23, 2010, and which claims the benefit of U.S. Provisional Application No. 61/361,717, filed Jul. 6, 2010, the contents of all of which are incorporated by reference herein.

BACKGROUND ART

Confocal line-scanning laser ophthalmoscopes are known per se. Reference can e.g. be made to U.S. Pat. No. 4,768,874 by Webb et all. describing such an apparatus. A line scanning laser ophthalmoscope (LSLO) is used for providing images of a scanned portion of an eye, the eye being scanned by a substantially line-shaped light beam. In general, the LSLO uses a light source, such as a laser or a superluminescent light emitting diode for generating a substantially collimated light beam. In order to perform the scanning operation, the LSLO is provided with a plurality of optical components or elements to process/convert the light source, to provide the light source in an appropriate shape to the eye, to process the reflected light received from the eye such that it can be processed by a detector. In general, the LSLO therefore comprises the following optical components:
- a first optical component for converting a substantially collimated light beam to a line-shaped light beam;
- a beam separating element arranged to receive the line-shaped beam and separating the incoming line-shaped beam and the reflected light;
- a scanning element arranged to receive the line-shaped beam and displace the line-shaped beam to enable scanning an area of an object of interest (e.g. an eye retina).
- optics for focussing the scanning line-shaped beam to enter the eye, e.g. through the pupil, receiving the light reflected from the eye and focussing the received reflected light on a detector, e.g. a linear CCD array.

Various optical components such as lenses and focusing minors may be used in between these elements to improve the properties of the system.

In case a conventional LSLO is applied to examine a retina of a cataract patient or a patient having similar media opacities, it has been observed that it may be difficult to generate high quality images. Also, laser speckle degrades the image quality; lasers are commonly used in SLOs and LSLOs to create the collimated beam.

By contrast, the point-scan SLO does not suffer from these problems. Point scan SLOs (SLOs) are known per se. Reference can e.g. be made to U.S. Pat. No. 4,768,873 by Webb et all. describing such an apparatus. In a point-scan SLO two scanners are used—a fast and comparatively slow scanner. The fast scanner scans an illuminated point along a line on the retina, and de-scans the returning light to a point detector. A conventional Line SLO contains only one scanner (a comparatively slow scanner) and uses a line sensor.

SUMMARY OF THE INVENTION

In view of the above, it is an object of the present invention to provide an improved LSLO enabling an improved image quality by, at least partly eliminating the effects of laser speckle, and/or by, at least partly, eliminating the effects of (moderate) forms of cataract or other media opacities when examining patients having such opacities. This and other objects are realised, according to a first aspect of the invention, by a line-scanning ophthalmoscope, comprising:
- a light source to provide a light beam to an object of interest;
- a beam separating device to receive the light beam, provide the light beam to a scanning device and substantially separate the light beam and a returning light beam from the object of interest;
- a scanning device to direct the light beam to the object of interest for scanning the object of interest with a line-shaped light beam in a scanning direction; to receive the returning light beam from the object of interest; and to direct at least part of the returning light beam towards a detector;
- a further scanning device to convert the light beam to the line-shaped light beam for scanning the object of interest by displacing the light beam in a direction substantially perpendicular to the scanning direction, and wherein the returning light beam from the object of interest is not de-scanned by the further scanning device.

The novel LSLO of the present invention can be seen as a hybrid between the traditional point SLO and the Line SLO, combining advantages of both instruments. Confocal scanning laser ophthalmoscopes (SLOs) are known per se and provide, as known, an advantage with respect to obtainable contrast due to the application of a point or point-like illumination of an object of interest instead of using a spatially extended light source. In an SLO, a laser spot is typically scanned across the retina and the reflected light is de-scanned and imaged onto a sensitive single point detector, such as, but not limited to, an avalanche photo-diode. Such a flying spot optical design, which incorporates a confocal detector, greatly reduces stray light, and therefore enhances the image's contrast. In addition, this method allows the use of near infrared light for imaging the retina, which may further reduce discomfort to the patient.

In an SLO, each point on the retina is only illuminated very briefly. A very bright source of illumination must, therefore, be used to obtain a sufficient level of exposure despite the short exposure time. A laser source is typically used as they are typically the only sources capable of delivering the required high brightness.

In order to increase the pixel data rate and to reduce complexity and costs, line-scanning laser ophthalmoscopes have been developed, employing a line-shaped light beam for imaging an object of interest, e.g. an eye, by scanning a thin line of light across the retina, de-scanning the returning light and subsequently imaging this light on a line detector. It has been observed that by using this method most of the confocality of a point scan can still be retained. As a consequence, line scan images may have, thanks to their confocality, a much higher contrast compared to e.g. the area-based illumination of a fundus camera. Furthermore, thanks to their inherent short focal distance, such confocal systems have the ability to image 'slices' of an object at various depths and thus create a 3D topographic image.

Another advantage when scanning a line across the retina instead of a point, is that only one slow scanner is required instead of requiring both a slow and a (often noisy and expensive) fast scanner, and the optical path of the camera system can be much shorter. Therefore optics, electronics and mechanics can be simplified, all of which contribute to a decrease in production costs, a decrease in scanner noise and a decrease in size.

An important drawback of conventional LSLO's is that the image quality may be comparatively poor when patients are examined who have cataract or other defects on the eye lens which may (partly) block or distort the applied light beam. Images from a 'spot SLO' are much less affected by such opacities and defects. The comparatively poor image quality of Line-SLOs can be explained by the fact that the line generating devices as applied in conventional LSLO's generate a 1-to-1 spatial correlation between the illumination intensity along the line-shaped light beam and the location of the defects in the entrance pupil.

The different behaviour of spot-SLO versus line-SLO is illustrated in more detail below in FIGS. 1a and b.

Another important drawback of the LSLO and SLOs in general, is laser speckle. Due to interference of the coherent laser light, a pattern of lighter and darker spots is superimposed on the retinal image of SLOs and LSLOs.

In the ophthalmoscope according to the present invention a light source is applied to provide a light beam to an object of interest. Such a light source can e.g. comprise a laser or an LED (light emitting diode) which can e.g. generate a collimated light beam. In the present document reference is sometimes made to the shape of a light beam (e.g. collimated or line-shaped). The light rays in a collimated light beam are substantially parallel to each other. In a line-shaped beam, there is a difference in the angle of the outer light rays between a horizontal and a vertical plane.

Wherever, within the present document, reference is made to the light beam or a light beam, such reference can either refer to the light beam as outputted by the light source or the light beam as obtained after a transformation, e.g. a cross-sectional transformation in a light generating device towards a line-shaped light beam.

In a preferred embodiment, the light source applied is a laser light source generating a collimated light beam. Compared to e.g. LED light sources, it can be mentioned that, at present, LED light source may possess an insufficient brightness as a point light source or, in case of superluminescent diodes, have the disadvantages of not being available in the visible range or, due to the broad frequency spectrum, have the disadvantage that the provision of an appropriate AR coating on the lenses is rendered more difficult. The ophthalmoscope according to the invention comprises a beam separating device to receive the light beam and provide the light beam to a scanning device of the ophthalmoscope. The beam separating device, which can e.g. comprise an element that is partially transmissive and partially reflective, a polarisation-based beam separator, a mirror with a hole, or a small minor around which part of the light is transmitted, is further arranged to substantially separate the light beam as received from the light source and a reflected light beam as received from the object of interest.

The ophthalmoscope according to the invention further comprises a scanning device for receiving a light beam e.g. from the beam separating device and directing the light beam to the object of interest for scanning the object of interest with a line-shaped light beam. The scanning device is further arranged to receive the reflected light beam from the object of interest; and to direct at least part of the reflected light beam towards a detector.

In the ophthalmoscope according to the first aspect of the invention, the light beam is converted to a line-shaped light beam by a further scanning device that displaces the light beam, at a comparatively high frequency, in a direction substantially perpendicular to the scanning direction; the scanning direction corresponding to the direction in which a line-shaped light beam is, during use, scanning the object of interest. In general, this scanning direction is substantially perpendicular to the direction into which the line of the line-shaped light beam extends.

In such arrangement, the further scanning device is thus used, instead of a conventional line generating device such as a cylindrical lens or a Powell lens to convert the light beam from the light source to a line-shaped light beam.

In an embodiment, the further scanning device is used at a frequency that is comparatively high compared to a scanning frequency for scanning the object of interest in the scanning direction.

In the ophthalmoscope according to the first aspect of the invention, the returning light beam is not de-scanned by the further scanning device, in contrast to a conventional SLO. As such, the returning light beam (having a line shape), can be received, optionally via one or more further optical components, by the scanning device, de-scanned by the scanning device and provided to a detector, e.g. a line detector.

In an embodiment, the further scanning device may further comprise a cylindrical lens, a Powell lens or an arrayed line generating device such as a lenticular lens array for expanding the line-shaped light beam in the direction substantially perpendicular to the scanning direction. In such arrangement, the line-shape light beam is actually generated in two stages, a first stage wherein the light beam is expanded by displacing the light beam in a direction perpendicular to the scanning direction and a second stage wherein the expanded light beam is further expanded in the direction substantially perpendicular to the scanning direction.

In an embodiment, the further scanning device is arranged to scan the object of interest at a fast scanning frequency that is comparatively high compared to a scanning frequency of the scanning device for scanning the object of interest. Typically, the (comparatively slow) scanning device will operate at a scanning frequency between 5-100 Hz whereas the (comparatively fast) scanning device will operate in a frequency range of 2.000-40.000 Hz.

In accordance with a second aspect of the present invention, there is provided line-scanning ophthalmoscope, comprising:
  a light source to provide a light beam to an object of interest;
  a beam separating device to receive the light beam, provide the light beam to a scanning device and substantially separate the light beam and a returning light beam from the object of interest;
  a scanning device to direct the light beam to the object of interest for scanning the object of interest with a line-shaped light beam; to receive the returning light beam from the object of interest; and to direct at least part of the returning light beam towards a detector;
  a line generating device to convert the light beam to the line-shaped light beam for scanning the object of interest, wherein the line generating device is an arrayed line generating device and
  a further scanning device for providing a displacement of the light beam or the line-shaped light beam in a direction substantially parallel to the line of the line-shaped light beam.

Compared to the ophthalmoscope according to the first aspect of the invention, the ophthalmoscope according to the second aspect comprises a line generating device, in particular an arrayed line generating device, in combination with a further scanning device.

In order to obtain a line-shaped light beam for scanning the object of interest, the ophthalmoscope according to the second aspect of the invention comprises an arrayed line generating device for converting an incoming light beam to an e.g. long and thin line-shaped light beam. As an example, such an arrayed line generating device can comprise an array of reflective of refractive ridges for converting a collimated light beam into a line-shaped light beam.

In accordance with the second aspect of the invention, the line-scanning ophthalmoscope further comprises a further scanning device for providing a displacement of the line-shaped light beam for scanning the object of interest in a direction substantially parallel to the line of the line-shaped light beam.

In an embodiment, the further scanning device is arranged to scan the object of interest at a fast scanning frequency that is comparatively high compared to a scanning frequency of the scanning device for scanning the object of interest. Typically, the (comparatively slow) scanning device will operate at a scanning frequency between 5-100 Hz whereas the (comparatively fast) scanning device will operate in a frequency range of 2.000-40.000 Hz.

Such a combination of a further scanning device and an arrayed line generating device provides, as will be explained in more detail below, an important advantage over conventional line generating devices such as a cylindrical lens or a Powell lens.

It is further worth noting that, as explained above with respect to the first aspect of the invention, the further scanning device may equally be applied to convert the light beam to the line-shaped light beam for scanning the object of interest and as such, may also be used without the arrayed line generating device.

It is worth noting that the further scanning device or the particular line generating device (i.e. the arrayed line generating device) can be applied at any suitable point in the light path (i.e. before, after of at the beam separation device) between the light source and the (comparatively slow) scanning device.

In an embodiment of the ophthalmoscope of the present invention, such a transformation occurs in between the beam separating device and the scanning device or on the beam separating device, by integrating the line generating device and the beam separating device. In such an embodiment of the ophthalmoscope according to the invention, the light beam as received by the beam separating device can e.g. be a collimated light beam, instead of a line-shaped beam, as found in known LSLOs. As such, a more compact design of the ophthalmoscope can be obtained. In addition, as will be understood by the skilled person, an accurate alignment or calibration of a line-shaping element (i.e. an optical element converting an incoming collimated light beam in to an outgoing line-shaped light beam) with respect to a further downstream element (e.g. the scanning element or the beam separation element), as required in known LSLOs, is no longer required. This may reduce the time to manufacture the apparatus or prepare the apparatus for operation.

As an alternative to integrating the line shaping functionality in the beam separating device, an embodiment of the ophthalmoscope according to the invention comprises the line generating device arranged in an optical path of the light beam between the beam separating device and the scanning device. As will be explained in more detail below, arranging the line-shaping functionality between the beam separating device and the slow scanning device instead of ahead of the beam separating device, enables to obtain improved optical properties of the ophthalmoscope.

As mentioned above, the line generating device as applied in the ophthalmoscope according to the second aspect of the invention is an arrayed line generating device, e.g. comprising an array of reflective of refractive ridges for converting a collimated light beam into a line-shaped light beam. These ridges may generally be of sub-millimeter dimensions. A specific ridge shape may be required to lead to the generation of a line-shaped light beam. Common ridge shapes include sinusoidal ridges, cylinder-shaped ridges and other curved profiles of both concave or convex curvature. Several types of these arrayed line generating devices are also known as lenticular lens arrays which are commonly used in stereo vision applications.

Applying an arrayed line generating device in combination with the further scanning device may provide particular advantages over a conventional line generating device. A conventional line generating device such as a cylindrical lens or a Powell lens generates a line for which there is a 1-to-1 correspondence between an entry position of a light beam on the line generating device and the position along the generated line-shaped light beam.

Within the meaning of the present, an arrayed line generating device is a line generating device whereby this 1-to-1 correspondence between an entry position of a light beam and a position of the light beam along the generated line-shaped light beam is no longer present. In an embodiment, the arrayed line generating device comprises a plurality of optical elements, arranged adjacent to each other in a direction substantially perpendicular to a direction of the incoming light beam, wherein each optical element is arranged to receive only part of the incoming light beam and convert the part of the incoming light beam as received to a line-shaped beam, the superposition of the line-shaped beams of the plurality of optical elements thus forming the line-shaped light beam. More details on various embodiments of such an arrayed line generating device are provided below. It is worth noting that the application of such an arrayed line-generating device (e.g. a lenticular lens array) may provide an improvement over known ophthalmoscopes as they enable the problem of image distortions to be eliminated or at least mitigated.

It can be noted that a similar effect, i.e. removing the 1-to-1 correspondence between an entry position of a light beam and a position of the light beam along the generated line-shaped light beam, may also be obtained by the further scanning device. As, such, as explained in more detail above in the first aspect of the invention, the further scanning device can be used instead of the arrayed line generating device for converting the light beam to the line-shaped light beam for scanning the object of interest.

The application of an arrayed line generating device and/or a further scanning device as in the present invention, results in a line-shaped light beam that, when provided, via an entrance pupil to a retina, provides a more uniform illumination of the retina. Phrased differently, due to the application of the arrayed line-generating device and/or the further scanning device, there is no longer a 1-to-1 correspondence between a position of the light beam as provided to the entrance pupil and a position on the retina. This is further explained in more detail below.

In case a coherent light source such as a laser source is used, the use of a lenticular lens array without a further (comparatively fast) scanning device instead of a single cylindrical lens, may adversely lead to interference effects in the illumination. As described in more detail below, such adverse effects can be eliminated using the further (comparatively fast) scanning device.

It is further worth noting that the ophthalmoscope according to the invention can be arranged to provide a plurality of line-shaped light beams, which can e.g. be derived from a single collimated light source, for scanning the object of interest.

As mentioned above and is explained in more detail below, the image quality of e.g. a retina image obtained by a conventional LSLO may be adversely affected by defects occurring on the lens of a patient's eye, mainly due to the 1-to-1 correspondence between an entry position of light beam on the line generating device (e.g. a cylindrical lens or a Powell lens) and the position along the generated line-shaped light beam. By using an arrayed line generating device as in the LSLO according to the second aspect of the invention, adverse effects of such defects on the image quality are mitigated. Such defects such as moderate forms of cataract may result in the appearance of dark lines in the retina image and could adversely affect the processing and analysis of the image obtained.

According to a third aspect of the invention, an LSLO may be provided with a further scanning device, a comparatively fast scanner, for displacing the light beam entering the pupil of a patient at a comparatively high frequency in a direction substantially perpendicular to a scanning direction of the LSLO. As such, according to a third aspect of the invention, there is provided a line-scanning ophthalmoscope, comprising:
  a light source to provide a light beam to an object of interest;
  a beam separating device to receive the light beam, provide the light beam to a scanning device and substantially separate the light beam and a returning light beam from the object of interest;
  a scanning device to direct the light beam to the object of interest for scanning the object of interest with a line-shaped light beam; to receive the returning light beam from the object of interest; and to direct at least part of the returning light beam towards a detector;
  a line generating device to convert the light beam to the line-shaped light beam for scanning the object of interest, and
  a further scanning device for in use displacing the light beam or the line-shaped light beam for scanning the object of interest in a direction substantially parallel to the line of the line-shaped light beam, at a frequency that is comparatively high compared to a scanning frequency for scanning the object of interest.

By displacing the light beam entering the pupil at a comparatively high frequency (compared to the line-scanning frequency of the LSLO), the adverse effects of defects on the patient's lens are smeared out over the image obtained thus resulting in a more uniform intensity which facilitates the processing and analysis of the image.

As such, the application of a further scanning device, which can e.g. operate at a comparatively high frequency compared to a scanning frequency as applied by the scanning device, in combination with a conventional line generating device such as a cylinder lens or powell lens, may provide a similar image quality improvement, compared to the use of an arrayed line generating device in combination with a further scanning device.

As a further advantage of this embodiment, it can be mentioned that any non-uniformity of the light beam (e.g. a speckle pattern of a laser beam) is equally smeared out rendering a more uniform intensity of the image obtained. Note that the same holds for the embodiments of the ophthalmoscope according to the first and second aspect of the invention as well.

It is further worth mentioning that, in an embodiment of the LSLO according to the present invention, both the arrayed line generating device and the further scanner or scanning device are applied. In such an embodiment, adverse interference effects in the illumination due to the use of e.g. a lenticular lens array instead of a single cylindrical lens in combination with a collimated light source may be mitigated. In such an embodiment, the further scanner may thus be mainly used for mitigating interference effects of the arrayed line generating device. However, the use of the further scanning device may also contribute in a more uniform light intensity on the object of interest which facilitates the processing and analysis of the image.

These and other aspects of the invention will be more readily appreciated as the same becomes better understood by reference to the following detailed description and considered in connection with the accompanying drawings in which like reference symbols designate like parts.

DESCRIPTION

Figure 1A:
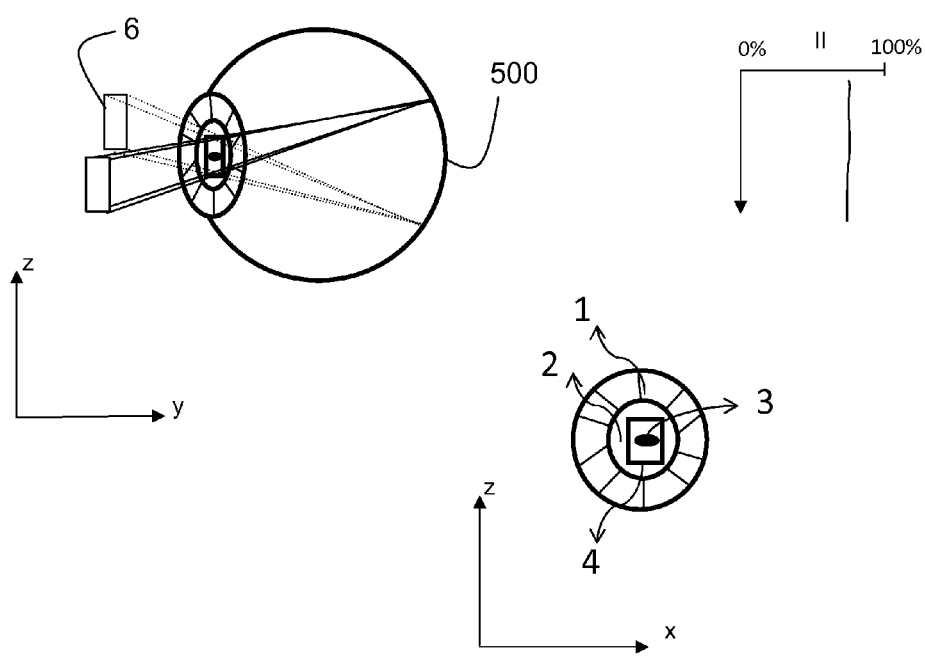
FIGS. 1A-1C schematically depict the different behaviour of a spot-SLO versus a line-SLO and an LSLO according to the invention.

FIG. 1A illustrates the imaging of a retina 500 with a spot SLO, wherein a beam of light (having a rectangular cross-section 6) illuminates only one retina point at each instant. A fast scanner that scans in one direction as well as a slow scanner that scans in a perpendicular direction inside the SLO are optically conjugated with the pupil plane, and therefore the light beam seems to 'pivot' around the center of the pupil as the beam is scanned across the retina. All the light rays in this beam enter the eye through the opening in the iris (1). Usually the light rays enter the eye only through a small section of the pupil; this is known as the 'entrance pupil' (4). As explained above, the entrance pupil is stationary during the scanning. Light reflected by the retina may exit the eye through any point in the eye pupil plane, however only light rays that exit the eye through a selected part of the pupil plane, will reach the detector. This part of the pupil is known as the 'exit pupil'(2). In FIG. 1a it can be seen that an opacity (3) in the eye lens will block part of the illuminated light as one point of the retina is imaged. However, the same amount of 'light blocking' is happening for all other points in the retina. The resulting image of the retina in will have a lower illumination level Il, indicated in the graph in the upper right corner of FIG. 1A, in the entire image, compared to imaging an object without the opacity.

Figure 1B:
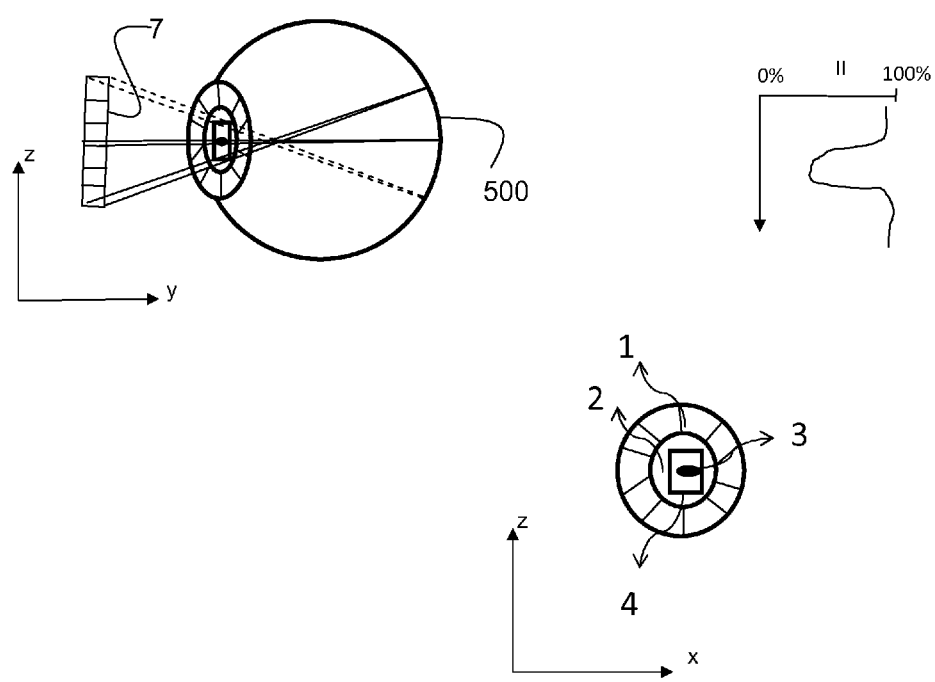

However in the case of a conventional Line SLO or LSLO, the situation is entirely different. At each instant, an entire line of the retina is illuminated. In an LSLO, a line-shaped light beam, schematically indicated by the cross-section 7, is used for scanning the retina. As is illustrated in FIG. 1B, each vertical position in the entrance pupil (4) corresponds to a specific location along the line. Phrased differently, the light entering the entrance pupil at a specific vertical position only ends up at specific vertical position on the retina, i.e. there is a 1-to-1 correspondence between a vertical position on the entrance pupil and a vertical position on the line illuminating the retina. As such, viewed from the retina, each point on the retina having a given vertical position, will only receive light from a light beam entering the entrance pupil at the corresponding vertical position on the entrance pupil. An opacity (3) in the entrance pupil (4) will thus cause a sharp decrease in the illumination level Il, indicated in the graph in the upper right corner of FIG. 1B, however only along only a small part of the line. This effect will create dark patches and dark stripes in the retina image and will render the processing and analysis of the image cumbersome.

Figure 1C:
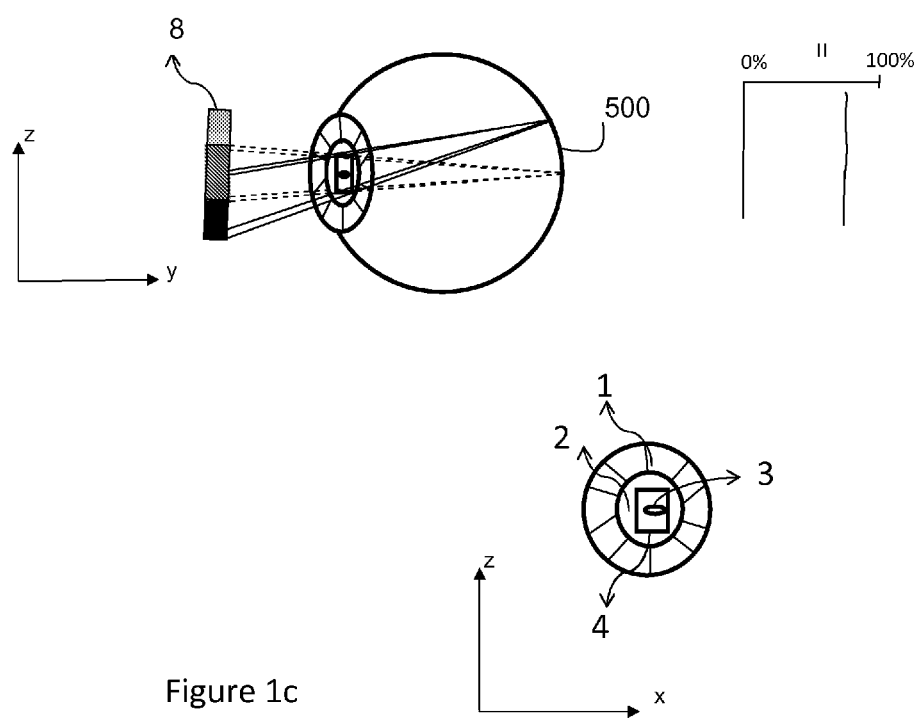

FIG. 1C illustrates a line-shaped light beam, schematically indicated by the cross-section 8, for scanning the retina as applied in the LSLO according to the invention. As illustrated in FIG. 1C, in accordance with the present invention, a large area of the entrance pupil is used to illuminate each point on the line, compared to just a single thin line in FIG. 1B. Therefore there is no longer a 1-1 correspondence between a point or opacity in the entrance pupil and a location along the illuminated line. As will be explained in more detail below, this can be realized in accordance with the present invention by applying an arrayed line generating device or a further scanning device or a combination thereof.

Figure 1D:
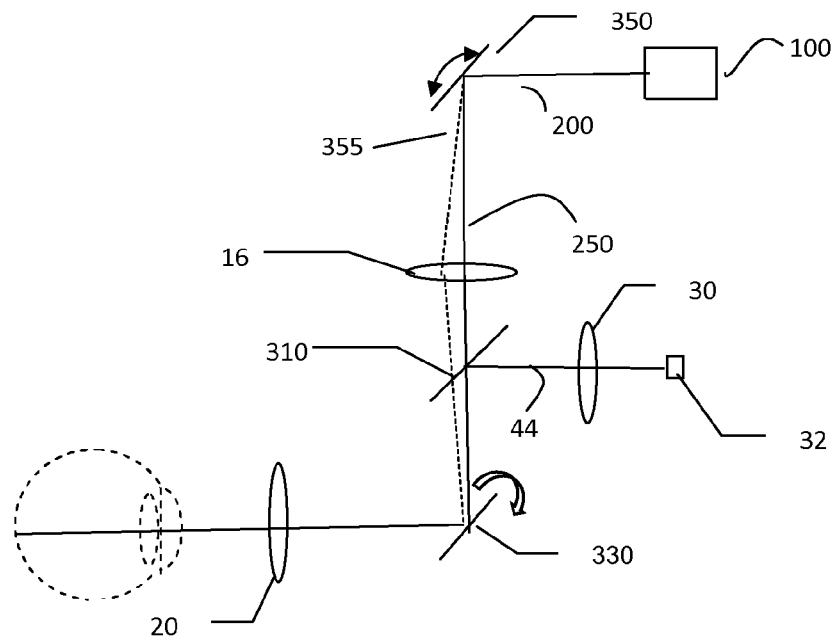
FIGS. 1D-1E schematically depict a first embodiment of a line-scanning laser ophthalmoscope according to the invention.

FIG. 1D is a schematic plan view of a first embodiment of a confocal, line scanning ophthalmoscope according to the invention. The confocal, line scanning ophthalmoscope comprises a light source 100 for providing a substantially collimated light beam 200 to a comparatively fast scanning device 350 (also referred to as the further scanning device), arranged to convert the collimated light beam 200 to a line-shaped light beam 250. In the embodiment as shown, the scanning device 350 is arranged to displace the line-shaped light beam in a direction substantially perpendicular to the scan direction of slow scanning device 330 as schematically indicated by the light beam 355. Typical scanning frequencies of the scanner or scanning device and further scanner or scanning device are between 5-100 Hz for the slow scanner and 2.000-40.000 Hz for the fast scanner, i.e. the further scanning device 350.

The line shaped light beam is subsequently provided, via a first optical element 16 to a beam separating element 310 which subsequently provides the light beam to a comparatively slow scanning device 330. In the optical path between the beam separating element 310 and the scanning device 330, a second optical element (not shown) can be provided for projecting the beam separating element 310 onto the scanning device 330. Such an optical element, e.g. a lens, may facilitate having the beam separating device 310 conjugated with the corneal plane and having the scanning device 330 conjugated with the pupil plane. The scanning device 330 provides in a scanning of an area of interest on an eye 21 via a third optical element 20. The scanning is performed in a direction substantially perpendicular to the line of the line-shaped light beam. Part of the light that impinges the eye 21 will be reflected by the retina 500 forming a reflected light beam which can be received by the scanning device 330 and directed towards the beam separating element 310. Due to the use of the comparatively fast scanning device, a comparatively uniform illumination of the retina can be obtained, even when an opacity on the entrance pupil would be present.

Subsequently, a reflected beam reflected from the object of interest (i.e. the eye 21) is de-scanned by the scanning device 330, provided to the beam separating element 310 and subsequently provided to a detector 32 via a fourth optical element 30. The beam separating element 310 is arranged in the optical path of the incoming light and the reflected or returning light. The beam separating element thereby separates the incoming light (i.e. the line shaped light beam 250) and the reflected, returning light beam 44 (which is, in the example as shown, deflected toward the detector 32). Note that, in the arrangement as shown, the returning light beam is not de-scanned by the comparatively fast scanning device 350.

Figure 1E:
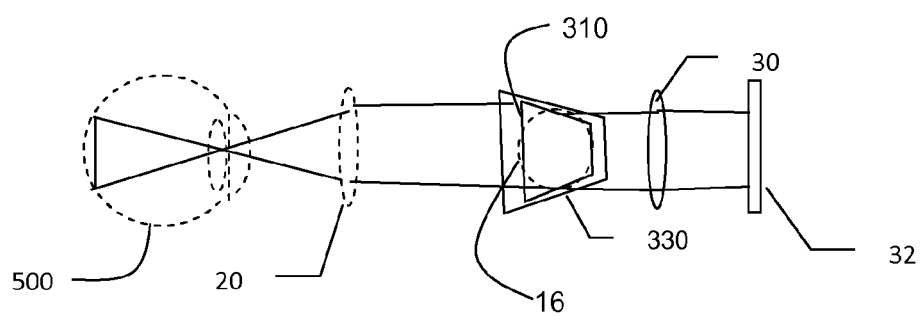

FIG. 1E is a schematic side view of the line scanning ophthalmoscope of FIG. 1D, showing the scanning device 330, the first optical element 16, the second optical element 20, the beam separating element 310, a third optical element 30 and the detector 32 from a side view. Note that some of the optical elements such as 16, 20 or 30 may consist of several optical elements such as lenses or focusing mirrors, forming an optical sub-system.

Figure 2:
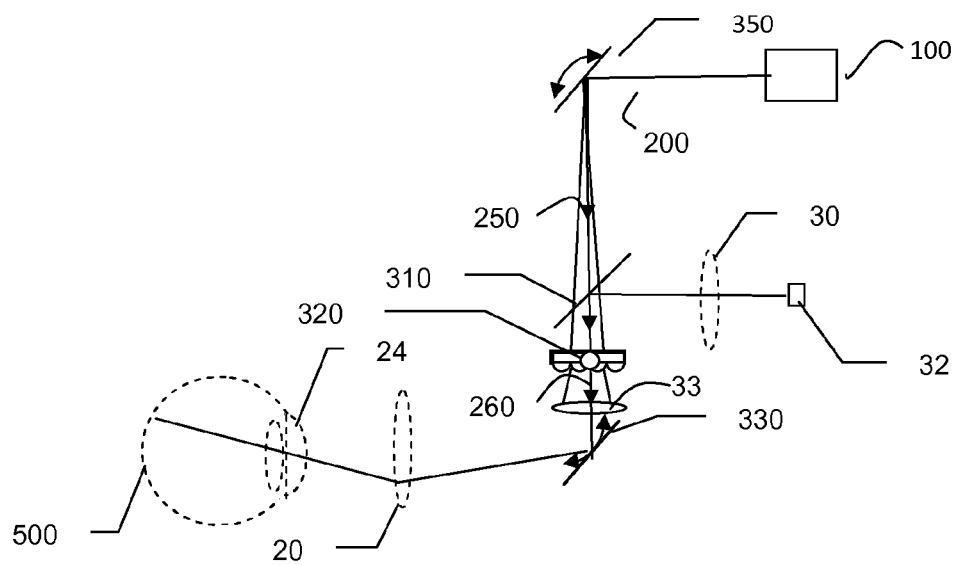
FIG. 2 schematically depicts a second embodiment of a line-scanning ophthalmoscope according to the present invention.

In FIG. 2, a second embodiment of an ophthalmoscope according to the invention is schematically depicted.

The ophthalmoscope as shown comprises a light source 100 arranged to provide a substantially line shaped light beam to a beam separating device 310 (via a comparatively fast scanning device 350, similar to the device as explained above) arranged to receive the light beam 200 (which is converted to a line-shaped light beam by the scanning device 350) and substantially separate the light beam 250 and a reflected or returning light beam (not shown), reflected from an object of interest, such as the retina 500 of an eye. As a beam separation device 310, several options exist. The beam separation device 310 can e.g. comprise a turning minor or a turning prism or a strip mirror. The beam separating device can e.g. comprise a minor having a comparatively small hole in a center of the mirror enabling an incoming beam (e.g. the line shaped beam 250) to pass the separating device (e.g. towards a scanning device 330), whereas a reflected beam, having a cross-section which can be substantially larger, is reflected by the beam separating device, e.g. towards a detector.

As schematically shown in FIG. 2, the collimated light beam originating from the source 100 is received by a comparatively fast scanning device 350, and subsequently by a line generating device 320 of the ophthalmoscope, e.g. an arrayed line generating device such as a lenticular lens array, the optical component 320 being arranged to convert the line shaped light beam 250 as received by the beam separation device 310 to an expanded line-shaped light beam 260 for scanning the object of interest. The line shaped light beam 260 is further received by a scanning device 330 which directs the line-shaped light beam 260 to an object of interest (e.g. an eye 500) in order to scan a portion of the object of interest in a direction substantially perpendicular to the line. Note that, as explained with respect to FIG. 1D, the ophthalmoscope as shown in FIG. 2 may be provided with an optical element 33 in the optical path between the beam separating element 310 and the scanning device 330 for projecting the beam separating element 310 onto the scanning device 330. The line generating device 320 as schematically depicted can e.g. comprise one or more lenses, e.g. cylindrical lenses for converting a collimated light beam to a line-shaped light beam or beams. As an alternative, the device 320 can comprise an array of narrow reflective or refractive ridges for converting the collimated light beam to a line-shaped light beam. As a third example, the line generating device can comprise a single Powell lens or a pair or Powell lenses separated by a gap to obtain a line-shaped light beam or beams. In order to convert the collimated light beam to a line-shaped light beam, the line generating device may also comprise a holographic optical element.

The line generating device 320 can e.g. be positioned just in front of the scanning device 330 and can be provided with a central hole for transmitting the part of light reflected by the retina that is to remain unaffected by the workings of the line generating device. This hole may be of any geometric shape (round, oval etc) or can be in the form of an elongated shape such as a slot. Furthermore, the line generating device may consist of two or more parts, spatially separated in the plane substantially perpendicular to the beam propagation direction. In this respect, it is worth noting that, in an embodiment, the line generating device is arranged to provide a pair of line-shaped light beams for scanning the object of interest. In such an arrangement, the pair (or, in general, the plurality) of light beams may enter the object of interest on different locations. As such, the adverse effects of defects on the patient's eye lens (occurring at particular locations on the eye lens) may be averaged out over the image obtained due to the application of more than one light beam entering the object of interest. As a result, the effects of the defects of the patient's eye on the image obtained from the LSLO may be mitigated, which facilitates the processing and analysis of the image.

With respect to the application of the line generating device 320 in an optical path between the beam separation device 310 and the scanning device 330, it is worth mentioning that such an arrangement, compared to conventional arrangements provide the advantage that the line-shape generation is brought closer to the scanning component. As a result, the conjugated focus of the line-shaped light beam can be brought on the eye lens instead of being in front of it.

Figure 3:
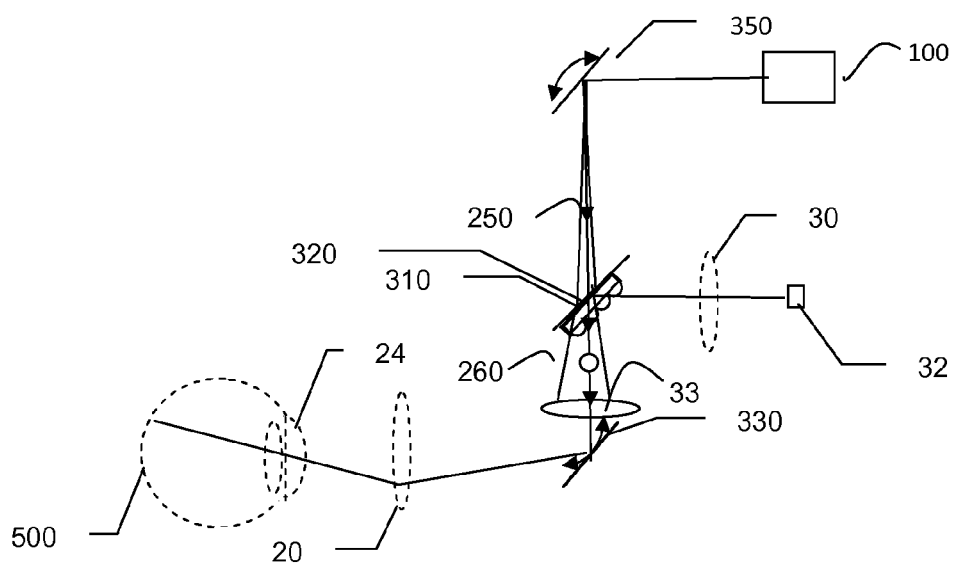
FIG. 3 schematically depicts a third embodiment of a line-scanning ophthalmoscope according to the present invention.

In FIG. 3, a third embodiment of the ophthalmoscope according to the present invention is schematically depicted which can provide comparable advantages as the first and second embodiment. Compared to the arrangement shown in FIG. 2, the ophthalmoscope as schematically shown does not comprise a separate line generating device arranged in an optical path between the beam separating device 310 and the scanning device 330. Instead, an arrayed line generating device 320 is mounted to the beam separating device 310 such that the required line-shaping functionality is integrated on the beam separating device 310. In the arrangement as shown, the beam separating device comprises the arrayed light generating device 320 arranged to receive the incoming line shaped light beam 250 provided by the light source 100 and scanner or scanning device 350. The arrayed line generating device 320 as provided on the beam separating device can e.g. comprise a lenticular lens array. Further embodiments of the arrayed line-shaping element can e.g. include a plurality of hollow, narrow ridges (either reflective or refractive). Note that, as also shown in FIG. 2, the ophthalmoscope as shown in FIG. 3 may equally be provided with an optical element 33 in the optical path between the beam separating element 310 and the scanning device 330 for projecting the beam separating element 310 onto the scanning device 330.

By incorporating the line-shaping functionality in the beam separation device, an alignment of a separate line-shaping component relative to the beam separating device 310 is no longer required, thus facilitating the manufacturing process. In addition or alternatively, the incorporation of the line-shaping functionality may result in a more compact, thus less voluminous design of the ophthalmoscope.

Figure 4:
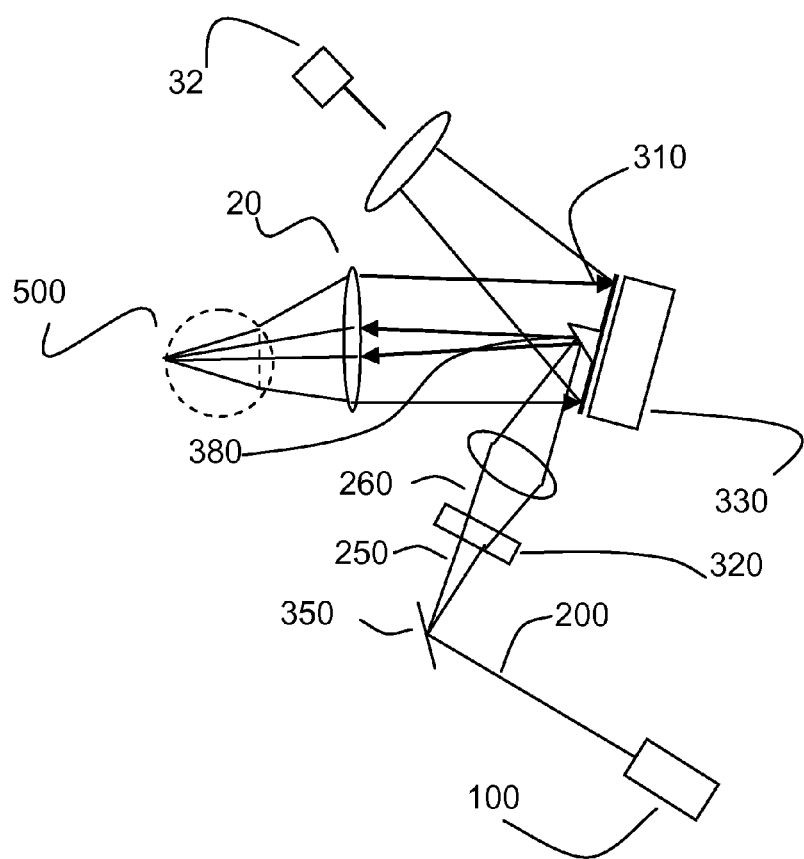
FIG. 4 schematically depicts a fourth embodiment of a line scanning ophthalmoscope according to the present invention.

In FIG. 4, yet another embodiment of an LSLO according to the invention is schematically depicted whereby the beam separating device is integrated with the scanning device. In the plan view of FIG. 4, a beam separating device 310 is mounted to a scanning device 330 such that the beam separating device 310 is rotated along with the scanning device 330 during scanning. In the embodiment as shown, a first (inner) section of the beam separating device 310 is provided with a reflective surface 380 arranged to receive a line-shaped beam from a light generating element 320. The reflected light beam is subsequently, via optical element 20, received by the object of interest 500. Reflected beams from the object of interest are subsequently received by a second (outer) section 385 of the beam separating device 310 and reflected towards detector 32. As will be understood, other arrangements of the first and second section (receiving the light beam of the light source 100 via comparatively fast scanner 350 and the light beam of the object of interest respectively) can be considered as well.

As already described above, in an embodiment, the arrayed line generating device as applied in the ophthalmoscope according to the first aspect of the invention can comprise an array of reflective or refractive ridges for converting the light beam into a line-shaped light beam. The ridges of such an arrayed line generating device will generally be of sub-millimeter dimensions. A specific ridge shape may be required to lead to the generation of a line as the output beam. Common ridge shapes include sinusoidal ridges, cylinder-shaped ridges and other curved profiles of both concave or convex curvature, also known as lenticular lens arrays which are commonly used in stereo vision applications.

Figure 5A:
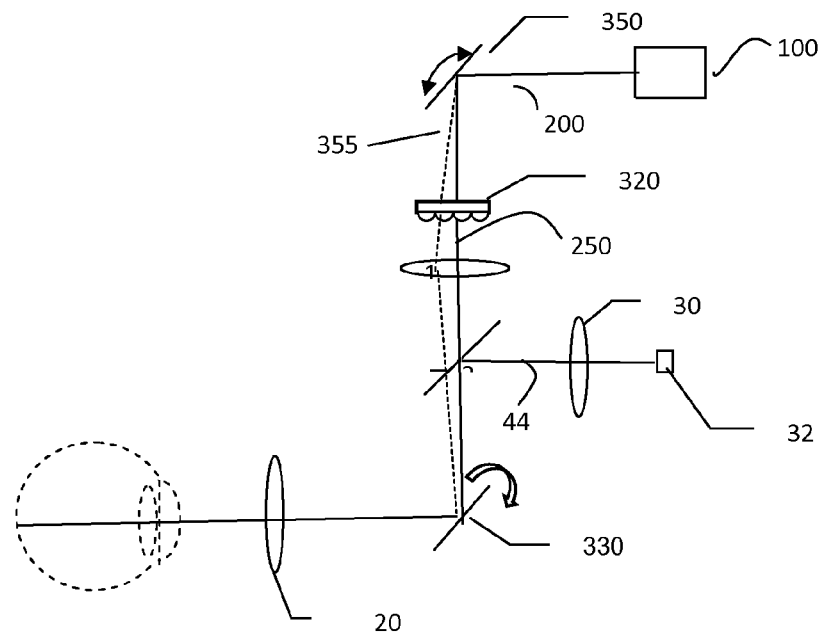
FIGS. 5A and 5B schematically depict a fifth embodiment of a line scanning ophthalmoscope according to the invention.

In an embodiment of the ophthalmoscope according to the invention, a further fast scanning device is provided for displace the light beam entering the object of interest at a comparatively high frequency in a direction substantially perpendicular to a scanning direction of the LSLO, i.e. in a direction substantially parallel to the line of the line-shaped light beam. Such a fast scanning device may be used in an LSLO according to the second aspect of the invention. Such an LSLO may e.g. have a conventional line generating device such as a cylindrical lens or a Powell lens as an alternative to the use of the arrayed line generating devices of the configurations described above in FIGS. 1D-4. However, the further scanning device may also be used to further complement the arrayed line generating devices as described above. A preferred embodiment that combines a fast scanning device and an arrayed line generating device is schematically depicted in FIG. 5a. Compared to the embodiment shown in FIG. 1D, the LSLO as schematically shown in FIG. 5a further comprises a line generating element 320. In the embodiment as shown, the scanning device 350 is arranged to displace the line-shaped light beam 355 in a direction substantially perpendicular to the scan direction of slow scanning device 330. Typical scanning frequencies of the scanner or scanning device and further scanner or scanning device are between 5-100 Hz for the slow scanner and 2.000-40.000 Hz for the fast scanner.

Figure 5B:
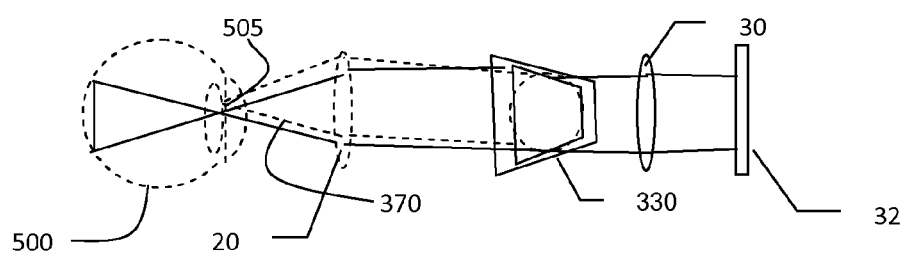

By displacing the line-shaped light beam by the further scanning device 350, as shown in the side view of FIG. 5b by the dotted lines 370, the point of entry 505 on the object of interest 500 of the light beam 355 can be altered at a comparatively high frequency (compared to the frame-scanning frequency of the LSLO in a direction perpendicular to the line of the line-shaped light beam 355, said scanning being provided by the scanning device 330). By displacing the point of entry on the object of interest (at comparatively high frequency during the scanning), adverse effects of any defects on the point of entry 505 are averaged or smeared out. This may result in an image having an improved quality as the appearance of artefacts on the image due to the defects on the point of entry can be reduced. Further, it should be noted that the further scanning device 350 as shown above may equally be applied downstream of the arrayed line generating device 320 or downstream of the scanning device 330.

As shown in FIGS. 1D and 1E, the further scanning device 350 as shown in FIG. 5a may be applied to generate a line-shaped light beam instead of the line generating device 320 as shown. As such, the line generating device 320 as shown in FIG. 5a can be considered optional since the further scanning device 350 can be used to generate the line-shaped beam. Note that, in such arrangement, the scanning and further scanning devices are arranged such that the returning light beam from the object of interest is not de-scanned by the further scanning device but rather, is directed towards the detector (e.g. via the scanning device and optionally the beam separating device 310.

Figure 6:
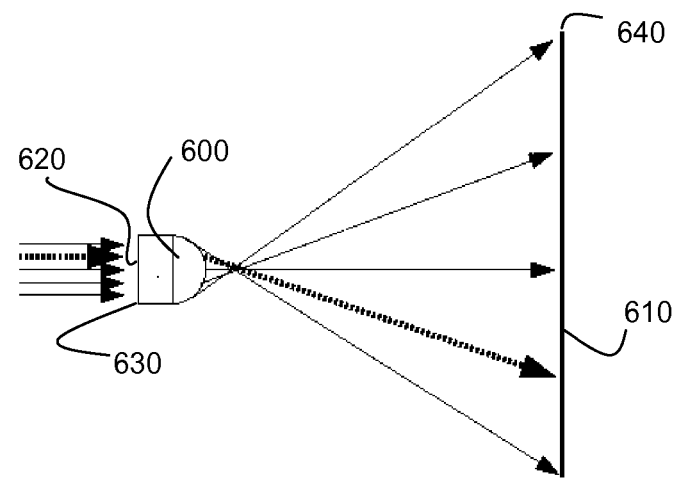
FIG. 6 schematically depicts a cylindrical lens and a lenticular lens array as can be applied as an arrayed line generating device in an ophthalmoscope according to the invention.
Figure 6:
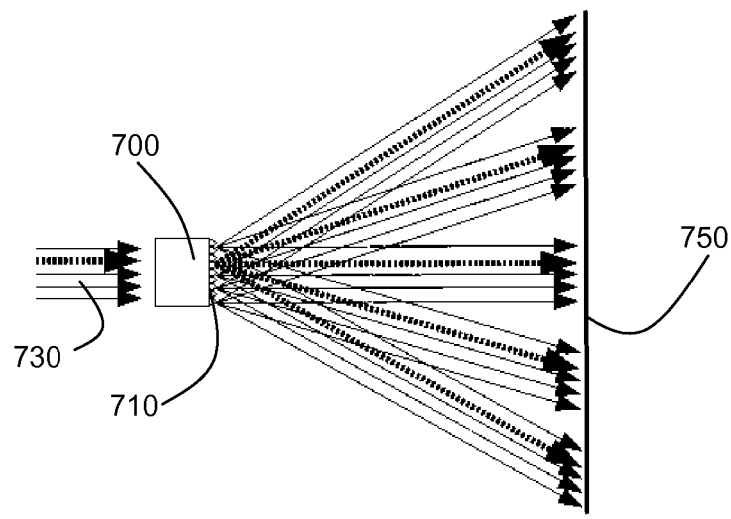

In FIG. 6, a comparison is made between the application of a cylindrical lens (top part) for generating a line shaped light beam and the application of an arrayed line generating device comprising an array of ridges for a generating a line shaped light beam. A conventional line generating device such as a cylindrical lens 600 or a Powell lens generates a line for which there is a 1-to-1 correspondence between the light at a position along the line 610 and the position 620 of the light entering the line-generating device: Light entering at the edge 630 of e.g. a cylinder lens 600 will contribute to the edge of the generated line 640, as can be seen in the top part of FIG. 6. The same holds for every other point on the line. As a consequence, should any part of the incoming light beam or the line generating device be blocked, then this will lead to an area of low brightness (or darkness) in the line, which will end up as a dark line or curve in the final image that is created when an object is scanned using the light shaped beam. When an array of line generating ridges in close proximity is applied, the 1 to 1 correspondence as mentioned is no longer present, as can be seen from the bottom part of FIG. 6. The line generating device 700 shown at the bottom of FIG. 6 comprises a large number of line generating elements (ridges) 710 arranged in close proximity with parallel alignment. As can be seen, even a small section of the input beam 730 (equal or larger than the array periodicity) will lead to an illumination over the full length of the line 750 generated. The combination of all such sections of the input beam 730 contribute to the entire brightness of the entire line length. As such, blocking a small part or small parts of the input beam will not lead to dark areas in the generated line but will merely result in a, comparatively small, overall decrease of intensity.

The focus of the line generating device is commonly approximately conjugated with the pupil plane in the eye. Any irregularities in or near the pupil plane such as in the eye lens or cornea can partially block the light rays from the line generating device. Therefore, by using a line generating device comprising an array of refractive or reflective ridges, also referred to as an arrayed line generating device, (as e.g. illustrated in FIG. 6) the problem of image distortions in line scanning laser ophthalmoscopes (LSLOs) can be eliminated or at least mitigated. As a result, by applying an arrayed line generating component, an LSLO can be constructed that is extremely robust against any media opacities that a patient may have, such as, for instance, cataracts (cortical cataract, nuclear cataract, etc), cataracta secundaria (nastaar), corneal imperfections (LASIK, herpes simplex), irregularities of the tear film and any floaters (deposits of organic matter) in the aqueous or vitreous humour. When using a 'conventional' line generating element, these media irregularities would lead to distortions in the image, appearing as dark stripes, curves and areas in the retinal image. When using an arrayed line generating device, these irregularities merely lead to an overall reduction of brightness without any spatial features.

Figure 7A:
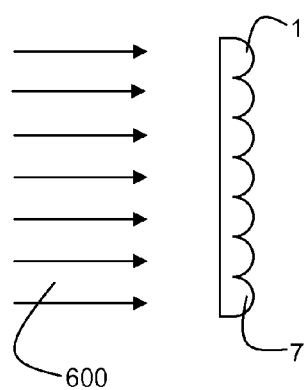
FIGS. 7a-7c schematically depict various embodiments of arrayed line generating device as can be applied in an ophthalmoscope according to the invention.
Figure 7B:
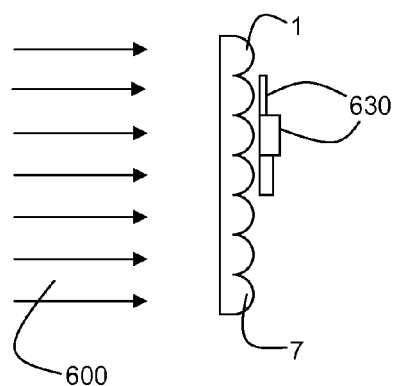
Figure 7C:
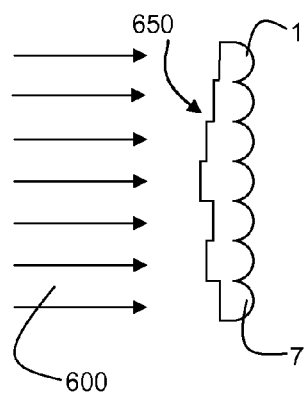

However, when a coherent light source such as a laser is used in combination with such an arrayed line generating device, this may lead to a pattern of interference fringes in the generated line. The spacing between these fringes depends on the spacing between the lenses or line generating elements in the array and the numerical aperture of the configuration. In FIG. 7a, such a periodic structured lens array (comprising 7 lenses 1 to 7) is schematically shown together with an incoming light beam 600. When interference fringes occur, and if the distance between the interference fringes is larger than one detector pixel in the same (optically conjugated) image plane, this interference pattern can lead to stripes in the image, either from direct imaging of the fringes that are projected onto the retina, or by aliasing of the fringes when the pixel size is not an integer multiple of the interference frequency. Several methods can be used to reduce these interference effects by spreading or averaging the interference pattern. These include 1) a phase modification method and 2) a scanning method:

1) The phase modification method makes use of phase differences between the individual lenses to achieve a reduction of the interference pattern. Altering the phase of the light passing through one of the lens elements effectively shifts the interference pattern by a small amount along the line. As such, when a sufficient number of different phase shifts can be provided the resulting illuminated line will consist of the sum of these shifts, and therefore the interference patterns can average each other out. An implementation of this method could, as schematically shown in FIG. 7b, e.g. involve placing an optical element comprising small transparent plates 630 of different thickness in front (or after) each lens, or integrating all such little plates into one plate with steps in thickness. Preferably, such a step-wise transmissive plate may be positioned in front of the lenticular array or even integrated in the array, the latter being illustrated in FIG. 7c whereby a front side 650 of the lenticular array has a step-wire varying thickness. As the required thickness variations may be comparatively small ~100-1000 nm depending on the wavelength of the light source, deposition or etching techniques may be applied in order to manufacture such a step-wise transmissive plate or front side 650. In another embodiment, such a 'phase plate' is rotated to provide even more spreading of the interference pattern.

2) The scanning method comprises the use of a fast scanning device which scans in a direction along the illuminated line, for instance as illustrated in FIGS. 2, 3, 4, 5a and 5b. When using a fast scanning device in combination with a line generating array, the interference fringes will move in the direction along the line. If the amplitude of the scan is at least as large as the distance between two interference fringes, the interference pattern can be averaged out during the exposure time of each imaged line, if the frequency of the scan is at least half the frequency of the line detector. The best results are achieved if the fast scanning frequency is an integer multiple or integer fraction of the exposure frequency of the line detector.

As a further advantage of this embodiment, it can be mentioned that any non-uniformity of the light beam (particularly the speckle pattern of a laser beam) is equally smeared out rendering a more uniform intensity and better resolution of the image obtained.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

The invention claimed is:

1. A line-scanning ophthalmoscope, comprising:
a light source to provide a light beam to an object of interest;
a beam separating device to receive the light beam, provide the light beam to a scanning device and substantially separate the light beam and a returning light beam from the object of interest;
a scanning device to direct the light beam to the object of interest for scanning the object of interest with a line-shaped light beam; to receive the returning light beam from the object of interest; and to direct at least part of the returning light beam towards a detector;
a line generating device to convert the light beam to the line-shaped light beam for scanning the object of interest, wherein the line generating device is an arrayed line generating device; and
a further scanning device for providing a displacement of the light beam or the line-shaped light beam in a direction substantially parallel to the line of the line-shaped light beam;
wherein the arrayed line generating device comprises an array of reflective or refractive ridges for converting the light beam to the line-shaped light beam.

2. The ophthalmoscope according to claim 1 wherein the light source is a laser light source.

3. The ophthalmoscope according to claim 1 wherein the arrayed line generating device is arranged to convert the light beam to a superposition of a plurality of line-shaped beams forming the line-shaped light beam.

4. The ophthalmoscope according to claim 1 wherein the line generating device is arranged in an optical path of the light beam between the beam separating device and the scanning device.

5. The ophthalmoscope according to claim 1 wherein the line generating device is arranged in an optical path of the light beam before the beam separating device.

6. The ophthalmoscope according to claim 1 wherein the array of reflective or refractive ridges is further provided with an optical element such as a transmissive plate having a step-wise varying thickness for generating distinct phase shifts to distinct light beams emanating from the array of ridges.

7. The ophthalmoscope according to claim 1 wherein the arrayed line generating device has a frontside having a step-wise varying thickness.

8. The ophthalmoscope according to claim 1 wherein the detector is a line sensor.

9. The ophthalmoscope according to claim 1, wherein the further scanning device is arranged to provide the displacement at a fast scanning frequency that is comparatively high compared to a scanning frequency of the scanning device for scanning the object of interest.

10. The ophthalmoscope according to claim 9 wherein an amplitude of the displacement is at least as large as a distance between two interference fringes of the arrayed line generating device.

11. The ophthalmoscope according to claim 10, whereby the detector is a line detector, and the fast scanning frequency is an integer multiple or integer fraction of an exposure frequency of the line detector.

12. The ophthalmoscope according to claim 1 wherein the arrayed line generating device is arranged to provide a plurality of line-shaped light beams for scanning the object of interest.

13. The ophthalmoscope according to claim 12 wherein the plurality of line-shaped light beams are arranged to, in use, enter the object of interest on different locations.

14. The ophthalmoscope according to claim 1 wherein the arrayed line generating device comprises a plurality of optical elements, each arranged to receive only part of the light beam.

15. The ophthalmoscope according to claim 1 wherein the arrayed line generating device comprises a plurality of optical elements arranged adjacent each other in a direction substantially perpendicular to a direction of the light beam.

16. A line-scanning ophthalmoscope, comprising:
a light source to provide a light beam to an object of interest;
a beam separating device to receive the light beam, provide the light beam to a scanning device and substantially separate the light beam and a returning light beam from the object of interest;
a scanning device to direct the light beam to the object of interest for scanning the object of interest with a line-shaped light beam; to receive the returning light beam from the object of interest; and to direct at least part of the returning light beam towards a detector;
a line generating device to convert the light beam to the line-shaped light beam for scanning the object of interest; and
a further scanning device for in use displacing the light beam or the line-shaped light beam for scanning the object of interest in a direction substantially parallel to the line of the line-shaped light beam, at a frequency that is comparatively high compared to a scanning frequency for scanning the object of interest.

17. The line-scanning ophthalmoscope according to claim 16 wherein the line generating device comprises a cylindrical lens or a Powell lens.

* * * * *